United States Patent
Sakai et al.

(10) Patent No.: US 6,468,992 B1
(45) Date of Patent: Oct. 22, 2002

(54) PHOSPHONIC ACID DIESTER DERIVATIVES

(75) Inventors: Yasuhiro Sakai; Kazuyoshi Miyata; Kenichi Kawamura; Yoshihiko Tsuda; Yasuhide Inoue, all of Naruto (JP)

(73) Assignee: Otsuka Pharmaceutical Factory, Inc. (JP)

( * ) Notice: Subject to any disclaimer, the term of this patent is extended or adjusted under 35 U.S.C. 154(b) by 0 days.

(21) Appl. No.: 09/674,145

(22) PCT Filed: Apr. 21, 1999

(86) PCT No.: PCT/JP99/02114

§ 371 (c)(1),
(2), (4) Date: Dec. 13, 2000

(87) PCT Pub. No.: WO99/55713

PCT Pub. Date: Nov. 4, 1999

(30) Foreign Application Priority Data

Apr. 24, 1998 (JP) .............................. 10-115536

(51) Int. Cl.⁷ .............................. C07F 9/40; C07F 9/58; C07D 213/75; A61K 31/44; A61P 31/10
(52) U.S. Cl. ........................... 514/89; 514/119; 546/22; 558/207
(58) Field of Search ..................... 558/70, 207; 546/22; 514/89, 119

(56) References Cited

FOREIGN PATENT DOCUMENTS

JP          09286792 A     11/1997

*Primary Examiner*—Taofig Solola
*Assistant Examiner*—Kamal Saeed
(74) *Attorney, Agent, or Firm*—George W. Neuner, Esq.; Edwards & Angell, LLP

(57) ABSTRACT

The present invention provides novel phosphonic acid diester derivatives useful as medicines. The phosphonic acid diester derivatives (1)

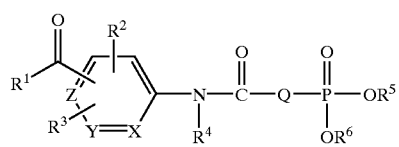

are represented by the general formula:

wherein $R^1$ represents amino group, N-lower alkylamino group, N-lower alkenylamino group, or the like;

$R^2$ and $R^3$ represent hydrogen atom, lower alkyl group, halogen atom, lower alkoxy group, or the like;

$R^4$ represents hydrogen atom, lower alkyl group or phenyl (lower)alkyl group;

$R^5$ and $R^6$ represent lower alkyl group;

X, Y and Z represent that all of them are carbon atoms or one of them is nitrogen atom and the other two are carbon atoms;

Q represents a single bond or alkylene group;

or the pharmacologically acceptable salts thereof.

24 Claims, No Drawings

PHOSPHONIC ACID DIESTER DERIVATIVES

This application is a 371 of PCT/JP99/02114 filed on Apr. 21, 1999.

TECHNICAL FIELD OF THE INVENTION

The present invention relates to novel phosphonic acid diester derivatives and agents for the prophylaxis or treatment of diabetes containing the same.

BACKGROUND OF THE INVENTION

The derivatives of the present invention are novel compounds which have not been so far described in the literature.

DISCLOSURE OF THE INVENTION

The present invention provides novel derivatives represented by the following general formula (1):

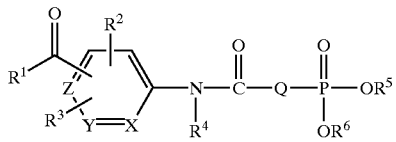

(1)

wherein $R^1$ represents an amino group, a N-lower alkylamino group, a N-lower alkenylamino group, a N-phenylamino group, a N-phenylamino group whose benzene ring is substituted with 1 or 2 groups being elected from halogen atom and lower alkoxy group, a N-phenyl(lower)alkylamino group, a N,N-di(lower)alkylamino group or a 4-lower alkylpiperazinyl group;

$R^2$ and $R^3$ each independently represent a hydrogen atom, a lower alkyl group, a halogen atom, a lower alkoxy group, a nitro group, an amino group, a N-lower alkylsulfonylamino group or a N-lower alkanoylamino group;

$R^4$ represents a hydrogen atom, a lower alkyl group or a phenyl(lower)alkyl group;

$R^5$ and $R^6$ each independently represent a lower alkyl group;

X, Y and Z each are carbon atoms or one of them is a nitrogen atom and the other two are carbon atoms;

Q represents a single bond or an alkylene group;
or pharmacologically acceptable salts thereof.

The phosphonic acid diester derivative or the pharmacologically acceptable salts thereof of the present invention have blood glucose-lowering activities and are typically useful, for example, as agents for the prophylaxis or treatment of diabetes.

That is to say, the present invention relates to:

(1) Phosphonic acid diester derivative represented by the general formula:

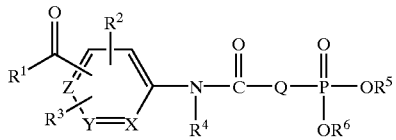

(1)

wherein $R^1$ represents an amino group, a N-lower alkylamino group, a N-lower alkenylamino group, a N-phenylamino group, a N-phenylamino group whose benzene ring is substituted with 1 or 2 groups being selected from a halogen atom and a lower alkoxy group, a N-phenyl(lower)alkylamino group, a N,N-di(lower)alkylamino group or a 4-lower alkylpiperazinyl group;

$R^2$ and $R^3$ each independently represent a hydrogen atom, a lower alkyl group, a halogen atom, a lower alkoxy group, a nitro group, an amino group, a N-lower alkylsulfonylamino group or a N-lower alkanoylamino group;

$R^4$ represents a hydrogen atom, a lower alkyl group or a phenyl(lower)alkyl group;

$R^5$ and R6 each independently represent a lower alkyl group;

X, Y and Z each are carbon atoms or one of them is nitrogen atom and the other two are carbon atoms;

Q represents a single bond or an alkylene group;
or the pharmacologically acceptable salts thereof, (2) The phosphonic acid diester derivative or the pharmacologically acceptable salt thereof described in the aforesaid paragraph (1), wherein X, Y and Z are all carbon atoms, or X is nitrogen atom and both Y and Z are carbon atoms, (3) The phosphonic acid diester derivative or the pharmacologically acceptable salt thereof described in the aforesaid paragraph (2), wherein X, Y and Z are all carbon atoms, (4) The phosphonic acid diester derivative or the pharmacologically acceptable salt thereof described in the aforesaid paragraph (3), wherein the derivative is represented by the general formula:

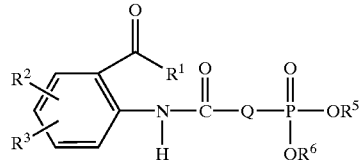

wherein $R^1$, $R^2$, $R^3$, $R^5$, $R^6$ and Q have the same meanings as set forth above, (5) The phosphonic acid diester derivative or the pharmacologically acceptable salt thereof described in the aforesaid paragraph (4), wherein $R^2$ and/or $R^3$ is a lower alkyl group, a halogen atom or a nitro group, (6) The phosphonic acid diester derivative or the pharmacologically acceptable salt thereof described in the aforesaid paragraph (5), wherein Q is trimethylene group, (7) The phosphonic acid diester derivative or the pharmacologically acceptable salt thereof described in the aforesaid paragraph (6), wherein $R^2$ is a halogen atom and $R^3$ is a hydrogen atom or a halogen atom, (8) The phosphonic acid diester derivative or the pharmacologically acceptable salt thereof described in the aforesaid paragraph (7), wherein the derivative is one selected from diethyl 3-(N-(3,5-dichloro-2-(N-methylcarbamoyl)phenyl)carbamoyl)propylphosphonate, diethyl 3-(N-(4,6dichloro-2-(N-methylcarbamoyl)phenyl)carbamoyl)propylphosphonate and diethyl 3-(N-(3-chloro-2-(N-phenylcarbamoyl)phenyl)carbamoyl)propylphosphonate, (9) An agent for the prophylaxis or treatment of diabetes containing at least one compound described in any of the aforesaid paragraphs (1) to (8) as active ingredient together with nontoxic carrier,

(10) Use of the compound described in any of the aforesaid paragraphs (1) to (8) for manufacturing a medicament for the prophylaxis or treatment of diabetes,

(11) The compound described in any of the aforesaid paragraphs (1) to (8) used for manufacturing a medicament for the prophylaxis or treatment of diabetes,

(12) A pharmaceutical composition comprising the compound described in any of the aforesaid paragraphs (1) to (8) and the pharmacologically acceptable carrier,

(13) The method of preventing or treating diabetes which comprises administering a treatment effective amount of the compound described in any of the aforesaid paragraphs (1) to (8) to a diabetic patient, and

(14) Blood glucose-lowering agent comprising the compound described in any of the aforesaid paragraphs (1) to (8).

Each group defined in the aforesaid general formula (1), representing phosphonic acid diester derivatives, is illustrated as follows. In the following description of this specification explaining the present invention, the term "phosphonic acid diester derivative or the pharmacologically acceptable salt thereof" is hereinafter referred to merely as "phosphonic acid diester derivative".

The term N-lower alkylamino group includes amino groups having a lower alkyl moiety that is a straight- or branched-chain alkyl group of 1 to 6 carbon atoms, for example, N-methylamino, N-ethylamino, N-propylamino, N-butylamino, N-pentylamino, N-hexylamino, and the like.

The term N-lower alkenylamino group includes amino groups having a lower alkenyl moiety that is a straight- or branched-chain alkenyl group of 2 to 6 carbon atoms, for example, N-vinylamino, N-allylamino, N-isopropenylamino, N-(3-butenyl)amino, N-(4-pentenyl) amino, N-(5-hexenyl)amino, and the like.

The term halogen atom includes, for example, a fluorine atom, a chlorine atom, a bromine atom, an iodine atom, and the like.

The term lower alkoxy group includes a straight- or branched-chain alkoxy group having 1 to 6 carbon atoms, for example, methoxy, ethoxy, propoxy, isopropoxy, butoxy, pentyloxy, hexyloxy, and the like.

The term N-phenyl(lower)alkylamino group includes N-alkylamino groups wherein the lower alkyl moiety that is a straight- or branched-chain alkyl group of 1 to 6 carbon atoms and wherein a hydrogen atom of the alkyl group is substituted with a phenyl group, for example, N-benzylamino, N-(1-phenylethyl)amino, N-(2-phenylethyl)amino, N-(3-phenylpropyl)amino, N-(4-phenylbutyl)amino, N-(5-phenylpentyl)amino, N-(6-phenylhexyl)amino, and the like.

The term N,N-di(lower)alkylamino group includes amino groups having two lower alkyl moieties, which can be the same or different, that are a straight- or branched-chain alkyl group of 1 to 6 carbon atoms, for example, N,Ndimethylamino, N,N-diethylamino, N,N-dipropylamino, N,N-dibutylamino, N,N-dipentylamino, N,N-dihexylamino, N-ethyl,N-methylamino, N-methyl,N-propylamino, and the like.

The term 4-lower alkylpiperazinyl group includes a piperazinyl group having a lower alkyl moiety that is a straight- or branched-chain alkyl group of 1 to 6 carbon atoms, for example, 4-methylpiperazinyl, 4-ethylpiperazinyl, 4-propylpiperazinyl, 4-butylpiperazinyl, 4-pentylpiperazinyl, 4-hexylpiperazinyl, and the like.

The term lower alkyl group includes a straight- or branched-chain alkyl group of 1 to 6 carbon atoms, for example, methyl, ethyl, propyl, isopropyl, butyl, isobutyl, tert-butyl, pentyl, hexyl, and the like.

The term N-lower alkylsulfonylamino group includes a sulfonylamino group having a lower alkyl moiety that is a straight- or branched-chain alkyl group of 1 to 6 carbon atoms, for example, N-methylsulfonylamino, N-ethylsulfonylamino, N-propylsulfonylamino, N-butylsulfonylamino, N-pentylsulfonylamino, N-hexylsulfonylamino, and the like.

The term N-lower alkanoylamino group includes an amino group having a lower alkanoyl moiety that is a straight- or branched-chain alkanoyl group of 2 to 7 carbon atoms, for example, N-acetylamino, N-propionylamino, N-butyrylamino, N-valerylamino, N-pivaloylamino, N-hexanoylamino, N-heptanoylamino, and the like.

The term phenyl(lower)alkyl group includes a phenyl group having a lower alkyl moiety that is a straight- or branched-chain alkyl group of 1 to 6 carbon atoms, for example, benzyl, 1-phenylethyl, 2-phenylethyl, 3-phenylpropyl, 4-phenylbutyl, 5-phenylpentyl, 6-phenylhexyl, and the like.

The term alkylene group refers to a straight- or branched-chain alkylene group of approximately 1 to 8 carbon atoms, for example, methylene, ethylene, ethylidene, trimethylene, tetramethylene, pentamethylene, hexamethylene, heptamethylene, octamethylene, and the like.

Examples of N-phenylamino group whose benzene ring is substituted with 1 or 2 groups selected from a halogen atom and a lower alkoxy group include N-(2-fluorophenyl)amino, N-(3-fluorophenyl)amino, N-(4-fluorophenyl)amino, N-(2-chlorophenyl) amino, N-(3-chlorophenyl)amino, N-(4-chlorophenyl)amino, N-(2- bromophenyl)amino, N-(3-bromophenyl)amino, N-(4-bromophenyl)amino, N-(4-iodophenyl)amino, N-(3,5-dichlorophenyl)amino, N-(2,3-dichlorophenyl)amino, N-(2,4-dichlorophenyl)amino, N-(2-methoxyphenyl)amino, N-(3-methoxyphenyl)amino, N-(4-methoxyphenyl) amino, N-(4-ethoxyphenyl)amino, N-(4-propoxyphenyl)amino, N-(4-butoxyphenyl)amino, N-(4-pentyloxyphenyl)amino, N-(4-hexyloxyphenyl)amino, N-(2,3-dimethoxyphenyl)amino, N-(2,4-dimethoxyphenyl) amino, N-(2,5-dimethoxyphenyl)amino, N-(2,6-dimethoxyphenyl)amino, N-(3,4-dimethoxyphenyl)amino, N-(3,5-dimethoxyphenyl)amino, and the like. Halogen atom and lower alkoxy group as substituents have the aforesaid significance.

The pharmacologically acceptable salts of phosphonic acid diester derivatives of the present invention include, for example, salts with inorganic acids such as hydrochloric acid, nitric acid and phosphoric acid, and salts with organic acids such as oxalic acid and fumaric acid.

Examples of compounds of the general formula (1) described above suitable for medicines, especially agents for the treatment of diabetes, include each compound belonging to any of groups (a) to (g).

(a) The phosphonic acid diester derivatives of the general formula (1), wherein X, Y and Z are all carbon atoms, or X is nitrogen atom and both Y and Z are carbon atoms.

(b) The phosphonic acid diester derivatives of the aforesaid item (a), wherein X, Y and Z are all carbon atoms.

(c) The phosphonic acid diester derivatives of the aforesaid item

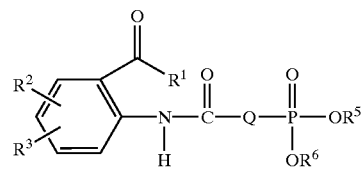

(b) which are represented by the following general formula:

wherein $R^1$, $R^2$, $R^3$, $R^5$, $R^6$ and Q have the same meanings as mentioned above, which are preferred compounds of the invention.

(d) The phosphonic acid diester derivatives of the aforesaid item (c), wherein $R^2$ and/or $R^3$ each is a lower alkyl group, a halogen atom or a nitro group, which are more preferred compounds of the invention.

(e) The phosphonic acid diester derivatives of the aforesaid item (d), wherein Q is trimethylene group, which also are more preferred compounds of the invention.

(f) The phosphonic acid diester derivatives of the aforesaid item (e), wherein $R^2$ is halogen atom and $R^3$ is hydrogen atom or halogen atom, which also are more preferred compounds of the invention.

(g) A more preferred phosphonic acid diester derivative of the aforesaid item (f) is a compound selected from diethyl 3-[N-[3,5-dichloro-2-(N-methylcarbamoyl)phenyl]carbamoyl]propylphosphonate, diethyl 3-[N-[4,6-dichloro-2-(N-methylcarbamoyl)phenyl]-carbamoyl]propylphosphonate and diethyl 3-[N-[3-chloro-2-(N-phenylcarbamoyl)phenyl]carbamoyl]propylphosphonate.

The phosphonic acid diester derivatives of the present invention can be prepared by various kinds of methods. The examples herein are described in detail using one of the following reaction schemes.

Reaction scheme -1

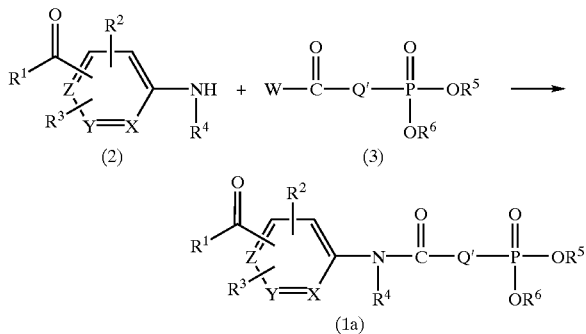

wherein $R^1$, $R^2$, $R^3$, $R^4$, $R^5$, $R^6$, X, Y and Z have the same meanings as mentioned above, Q' represents alkylene group, W represents halogen atom.

According to the procedure shown in Reaction scheme-1, a compound (1a) of the present invention can be obtained by reacting a compound (2) with an acid halide (3) in an inert solvent, in the presence of an acid acceptor. Both compounds (2) and (3) are compounds well known to those skilled in the art.

An inert solvent suitable for use in the reaction scheme as described above includes, for example, aromatic or aliphatic hydrocarbons such as benzene, toluene, xylene and petroleum ether, chain or cyclic ethers such as diethyl ether, 1,2-dimethoxyethane, tetrahydrofuran (THF) and 1,4-dioxane, ketones such as acetone, methyl ethyl ketone and acetophenone, and halogenated hydrocarbons such as dichloromethane, chloroform, carbon tetrachloride and 1,2-dichloroethane. The preferable examples of a suitable acid acceptor for use in the reaction scheme include tertiary amines such as triethylamine, pyridine, 4-dimethylaminopyridine, and the like.

The ratio between compound (2) and acid halide (3) employed in the above reaction is not limited specifically to, but is preferably from about an equimolecular amount to a small excess of the latter based on the former. It is preferable to employ usually an equimolecular amount to an excess of acid acceptor based on acid halide. The reaction proceeds either under cooling, at room temperature or under heating. It is preferable to carry out the reaction usually in the range of from 0° C. to the reflux temperature of the solvent and the reaction generally is completed in about 0.5 to 10 hours.

Reaction scheme -2

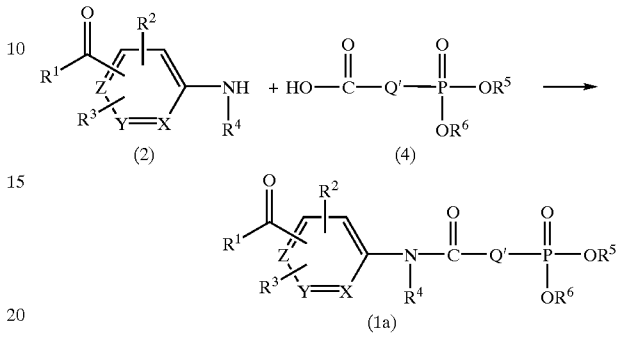

wherein $R^1$, $R^2$, $R^3$, $R^4$, $R^5$, $R^6$, X, Y, Z and Q' have the same meanings as mentioned above.

According to the procedure shown in Reaction scheme-2, a compound (1a) of the present invention can be obtained by reacting a compound (2) with a compound (4) in an inert solvent, in the presence of a condensing agent. Compound (4) is a compound well known to those skilled in the art.

A suitable inert solvent used in this reaction can be any of known aprotic solvents, for example, N,N-dimethylformamide (DMF), preferably, or the like. A suitable condensing agent includes, for example, N,N-dicyclohexylcarbodiimide (DCC), 1-hydroxybenzotriazole, N-hydroxysuccinimide, diethylphosphoryl cyanide, diphenylphosphoryl azide, and the like. The combined use of diethylphosphoryl cyanide and triethylamine is especially preferred.

The ratio between compound (2) and compound (4) for the use in the above reaction is, not limited in any way and may vary over a wide range, but preferably an equimolecular quantity to a small excess is used, more preferably about an equimolecular quantity of the latter based on the former. It is suitable to employ an equimolecular amount to an excess, preferably a small excess of the condensing agent based on compound (4). The reaction is carried out under the conditions ranging from cooling to near room temperature and is usually completed in about 0.5 to 2 hours.

Reaction scheme-3

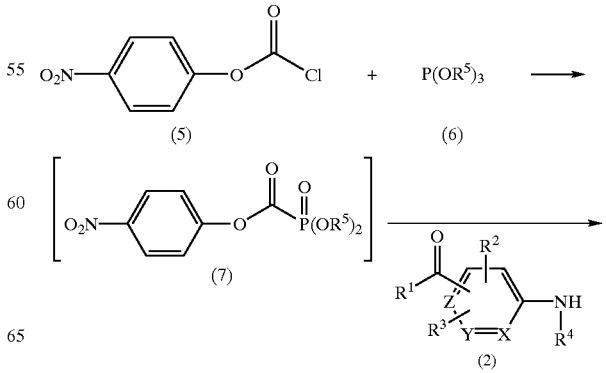

-continued

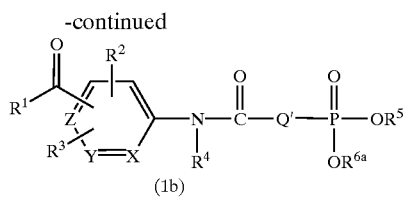

wherein $R^1$, $R^2$, $R^3$, $R^4$, $R^5$, X, Y and Z have the same meanings as mentioned above. $R^{6a}$ is the same as $R^5$.

According to the procedure shown in Reaction scheme-3, a compound (1b) of the present invention can be obtained by reacting p-nitrophenyl chloroformate (5) with trialkyl phosphite (6) in an inert solvent to yield a compound (7), which is not isolated, followed by reacting with a compound (2) in the same reaction mixture.

A suitable inert solvent for use in this reaction includes, for example, dichloromethane, chloroform, carbon tetrachloride, diethyl ether, THF, 1,4-dioxane, 1,2-dimethoxyethane, benzene, toluene, and the like.

The ratio of each compound used in the above reaction is not limited in any way and may vary over a wide range. It is preferable to use 1 to 1.2-fold molar quantities of p-nitrophenyl chloroformate (5) and trialkyl phosphite (6) based on compound (2), respectively.

The reaction between p-nitrophenyl chloroformate (5) and trialkyl phosphite (6) described above is carried out at room temperature to the reflux temperature of the solvent, preferably at the reflux temperature of a solvent, usually for 0.5 to 5 hours. The reaction between compound (7) and compound (2) is carried out at room temperature to the reflux 25 temperature of a solvent, preferably at near room temperature, usually for about 1 to 30 hours.

In the reaction between compound (7) and compound (2), an acid acceptor (for example, triethylamine, pyridine, N,N-dimethylaniline, N-methylmorpholine, or the like) can be added at equimolar (1x) to a small excessive molar quantities based on compound (2), if necessary.

The objective compound, i.e., the compound of the present invention, obtained by the procedures shown in the aforesaid reaction schemes is readily isolated and purified by conventional separation techniques, examples of which include adsorption chromatography, preparative thin-layer chromatography, recrystallization, solvent extraction, or/and the like. Compounds capable of forming salts of the aforesaid starting compounds (1) and (4) also can be used in the form of salts, and suitable examples of the salts include the aforesaid pharmacologically acceptable salts of such compounds.

Starting compounds (2), (3), (4), (5) and (6) are readily prepared by the methods well known to those skilled in the art.

Agents of the present invention for the prophylaxis or treatment of diabetes can be utilized in the form of general pharmaceutical preparations made by the use of the compounds represented by the above general formula (1) or the pharmacologically acceptable salts thereof as active ingredients, together with suitable nontoxic pharmaceutical carriers.

The aforesaid pharmaceutical carriers utilized in agents for the prophylaxis or treatment of diabetes of the present invention can be illustrated according to the usage form of the pharmaceutical preparations, for example, diluents or excipients such as commonly used bulking agents, extenders, binders, wetting agents, disintegrants, surfactants, lubricants, and the like, which can be selected appropriately by those skilled in the art in accordance with the dosage unit forms of the desired pharmaceutical preparations.

As the aforesaid dosage unit forms of the pharmaceutical preparations, various forms can be selected by those skilled in the art in accordance with the object of treatment, and the typical examples of the forms include tablets, pills, powder, liquid preparations, suspensions, emulsions, granules, capsules, suppositories, injectable preparations (liquids, suspensions, or the like), ointments, and the like.

In case of formulating in the form of tablets, suitable pharmaceutical carriers include, for example, excipients such as lactose, sucrose, sodium chloride, glucose, urea, starch, calcium carbonate, kaolin, crystalline cellulose, silicic acid and potassium phosphate, binders such as water, ethanol, propanol, simple syrup, glucose solution, starch solution, gelatin solution, carboxymethylcellulose, hydroxypropyl cellulose, methylcellulose and polyvinylpyrrolidone, disintegrants such as carboxymethylcellulose sodium, carboxymethylcellulose calcium, low-substituted hydroxypropyl cellulose, dried starch, sodium alginate, agar powder, laminaran powder, sodium bicarbonate and calcium carbonate, surfactants such as polyoxyethylene sorbitan fatty acid esters, sodium lauryl sulfate and stearic acid monoglyceride, disintegration inhibitors such as sucrose, stearin, cocoa butter and hydrogenated oil, absorption promoters such as quaternary ammonium base and sodium lauryl sulfate, moisturizers such as glycerol and starch, adsorbents such as starch, lactose, kaolin, bentonite and colloidal silica, lubricants such as purified talc, stearate, boric acid powder and polyethylene glycol, and the like. Further, tablets may be coated, if necessary, with usual coating materials to provide, for example, sugar-coated tablets, gelatin-coated tablets, enteric-coated tablets, film coating tablets, double-layer tablets, or multiple-layer tablets.

In case of formulating in the form of pills, suitable pharmaceutical carriers include, for example, excipients such as glucose, lactose, starch, cocoa butter, hardened vegetable oil, kaolin and talc, binders such as gum arabic powder, gum tragacanth powder, gelatin and ethanol, disintegrants such as laminaran and agar, and the like.

In case of formulating in the form of suppositories, suitable pharmaceutical carriers include, for example, polyethylene glycol, cocoa butter, higher alcohol, higher alcohol esters, gelatin, semisynthetic glyceride, and the like.

Capsules also can be prepared according to conventional methods well known to those skilled in the art, by mixing the compounds of the present invention with a variety of pharmaceutical carriers illustrated above, followed by filling hard gelatin capsules, soft gelatin capsules, or the like, with the mixture.

When prepared in the form of injectable preparations such as liquid preparations, emulsions and suspensions, these preparations are preferably sterile and isotonic to blood. In case of formulating into these forms, suitable diluents include, for example, water, ethanol, macrogel, propylene glycol, ethoxylated isostearyl alcohol, polyoxylated isostearyl alcohol, polyoxyethylene sorbitan fatty acid ester, and the like. The pharmaceutical preparations may contain enough sodium chloride, glucose or glycerol to prepare an isotonic solution and further usual solubilizing agents, buffer, soothing agents, and the like, may be added.

Further, the pharmaceutical preparations can contain coloring agents, preservatives, perfume, flavoring, sweetening agents, and the like, and other medicines, if necessary or desirable.

When prepared in the form of ointment such as paste, cream and gel, suitable diluents include, for example, white petrolatum, paraffin, glycerol, cellulose derivatives, polyethylene glycol, silicone, bentonite, and the like.

The amount of the compounds of the present invention (active ingredients) contained in the aforesaid pharmaceutical preparations is sufficient to provide the desired biological effect or a treatment effective amount. Thus, is not limited in any other way and may be selected appropriately by those skilled in the art from a wide range, preferably about 1 to 70 weight % of the pharmaceutical preparations.

The mode of administration of the aforesaid pharmaceutical preparations is not limited and may be determined readily by those skilled in the art according to a variety of pharmaceutical forms, the age, sex and other conditions of the patient, the degree of disease, and the like. For example, tablets, pills, liquid preparations, suspensions, emulsions, granules and capsules are administered orally, injectable preparations are administered intravenously, or intramuscularlly, intracutaneously, subcutaneously or intraperitoneally, soley or in combination with common replenishers such as glucose and amino acid, and suppositories are administered intrarectally.

The dosage of the aforesaid pharmaceutical preparations may be appropriately selected by those skilled in the art in accordance with the mode of administration, the age, sex and other conditions of the patient, the degree of disease, and the like. The compounds of the present invention (active ingredients) may generally be administered at a daily dose of from about 0.5 to 20 mg, preferably 1 to 10 mg per kg of body weight for an adult human, given in a single dose or in divided doses 2 to 4 times a day.

In the following section, preparation examples of compounds of the present invention are provided as examples in order to illustrate the present invention in more detail. Then, pharmacological tests on the compounds of the present invention and the pharmaceutical formulations of the compounds of the present invention are also provided. The $^1$H-NMR spectrum data of the compounds of the present invention (in the case of oily substances) which were obtained according to each production process, were measured by using $CDCl_3$ as a solvent and tetramethylsilane (TMS) as an internal standard.

BEST MODE FOR CARRYING OUT THE INVENTION

EXAMPLE 1

Diethyl 3-[N-[5-chloro-2-(N-methylcarbamoyl)phenyl]carbamoyl]propylphosphonate was prepared as follows.

4-(Diethoxyphosphoryl)butyric acid (12.13 g) was dissolved in dichloromethane (100 ml), to which a catalytic amount of DMF and thionyl chloride (6.44 g) were added successively at room temperature and the mixture was heated under reflux for 3 hours. Then, the reaction mixture was cooled to 0° C., to which a solution of 4-chloro-N-methylanthranilamide (9.99 g) in dichloromethane (50 ml) and pyridine (19.6 ml) was dropwise added at 0° C. and the mixture was stirred overnight at room temperature. The reaction mixture was washed successively with dilute hydrochloric acid and saturated saline solution, dried over anhydrous $MgSO_4$ and then concentrated under reduced pressure. The residue was purified by silica gel column chromatography (eluent; dichloromethane:methanol=20:1) to give a brown oily compound (14.81 g). The structure and melting point of the obtained compound are given in Table 1.

EXAMPLES 2 to 50

Each compound shown in Table 1 was obtained in the similar manner as Example 1. The structures and physical properties (melting points or NMR data) of those compounds are given in Table 1.

EXAMPLE 51

Diethyl N-[5-chloro-2-(N-methylcarbamoyl)phenyl]carbamoyl phosphonate was prepared as follows.

p-Nitrophenyl chloroformate (4.30 g) and triethyl phosphite 3.66 g) were dissolved in dry dichloromethane (20 ml) and the mixture as heated under reflux for 30 minutes.

Next the above reaction mixture was cooled to room temperature, to which N-methyl-2-amino-4-chlorobenzamide (3.69 g) and triethylamine (2.22 g) were added and the mixture was stirred at room temperature for 20 hours.

Water (50 ml) was added and the reaction mixture was extracted with chloroform. The chloroform layer was washed successively with saturated sodium bicarbonate aqueous solution (50 ml) and water (50 ml), then dried over anhydrous $Na_2SO_4$ and evaporated under reduced pressure. The residue was subjected to silica gel column chromatography (eluent; chloroform:ethyl acetate=1:1) and thus obtained crude crystals were recrystallized from ethyl acetate-n-hexane to give the desired compound (3.70 g) as colorless crystals. The structure and melting point of the obtained compound is given in Table 1.

EXAMPLES 52 to 56

Further, each compound shown in Table 1 was obtained in the similar manner as Example 1. The structures and physical properties (melting points or NMR data) of those compounds are given in Table 1.

In the following Table 1, Me, Et, i-Pr, Ph, Bn and Bu represent methyl, ethyl, isopropyl, phenyl, benzyl and n-butyl, respectively.

TABLE 1

| No | 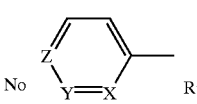 | $R^1$—C(O)— | Position of Substituent | $R^2$ | Position of Substituent | $R^3$ | Position of Substituent | $R^4$ | $R^5$ | $R^6$ | Q | Melting point (° C.) or NMR |
|---|---|---|---|---|---|---|---|---|---|---|---|---|
| 3 | 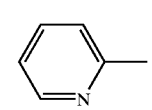 | 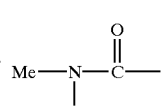 | 3 | H | — | H | — | H | Et | Et | —(CH$_2$)$_3$— | 73–75 |

TABLE 1-continued

| # | Structure | | | | | | | | | | | |
|---|---|---|---|---|---|---|---|---|---|---|---|---|
| 4 | Ph-N(Me)(H)-C(=O)- | 2 | Cl | 3 | H | — | H | Et | Et | —(CH$_2$)$_3$— | 118~120 |
| 5 | Ph-N(Me)(H)-C(=O)- | 2 | Cl | 4 | H | — | H | Et | Et | —(CH$_2$)$_3$— | 101.5~103 |
| 6 | Ph-N(Me)(H)-C(=O)- | 2 | Cl | 6 | H | — | H | Et | Et | —(CH$_2$)$_3$— | 127~128 |
| 7 | Ph-N(Me)(H)-C(=O)- | 2 | Cl | 3 | Cl | 5 | H | Et | Et | —(CH$_2$)$_3$— | '150~151.5 |
| 8 | Ph-N(Me)(H)-C(=O)- | 2 | Cl | 4 | Cl | 6 | H | Et | Et | —(CH$_2$)$_3$— | 149~150 |
| 9 | Ph-N(Me)(H)-C(=O)- | 2 | Cl | 3 | Cl | 6 | H | Et | Et | —(CH$_2$)$_3$— | 83~85 |
| 10 | Ph-N(Me)(H)-C(=O)- | 2 | F | 3 | H | — | H | Et | Et | —(CH$_2$)$_3$— | 92~95 |
| 11 | Ph-N(Me)(H)-C(=O)- | 2 | I | 4 | I | 6 | H | Et | Et | —(CH$_2$)$_3$— | 180~181 |
| 12 | Ph-N(Me)(H)-C(=O)- | 2 | Me | 3 | H | — | H | Et | Et | —(CH$_2$)$_3$— | 73~74 |
| 13 | Ph-N(Me)(H)-C(=O)- | 2 | Me | 4 | H | — | H | Et | Et | —(CH$_2$)$_3$— | 97~98 |
| 14 | Ph-N(Me)(H)-C(=O)- | 2 | Me | 6 | H | — | H | Et | Et | —(CH$_2$)$_3$— | 148.5~149.5 |
| 15 | Ph-N(Me)(H)-C(=O)- | 2 | NO$_2$ | 4 | H | — | H | Et | Et | —(CH$_2$)$_3$— | 97~98 |
| 16 | Ph-N(Me)(H)-C(=O)- | 2 | NO$_2$ | 5 | H | — | H | Et | Et | —(CH$_2$)$_3$— | 55~57 |

TABLE 1-continued

| | | | | | | | | | | | | |
|---|---|---|---|---|---|---|---|---|---|---|---|---|
| 17 | Ph-N(Me)-C(=O)- | 2 | MeSO$_2$NH | 4 | H | — | H | Et | Et | —(CH$_2$)$_3$— | 148~150 |
| 18 | Ph-N(Me)-C(=O)- | 2 | Me-C(=O)-NH | 4 | H | — | H | Et | Et | —(CH$_2$)$_3$— | 173~175 |
| 19 | Ph-N(Me)-C(=O)- | 2 | NH$_2$ | 4 | H | — | H | Et | Et | —(CH$_2$)$_3$— | 144~145 |
| 20 | Ph-N(Me)-C(=O)- | 2 | MeO | 6 | H | — | H | Et | Et | —(CH$_2$)$_3$— | 116~117 |
| 21 | Ph-N(Me)-C(=O)- | 2 | MeO | 4 | MeO | 5 | H | Et | Et | —(CH$_2$)$_3$— | NMR(3) |
| 22 | Ph-N(Et)-C(=O)- | 2 | Cl | 4 | H | — | H | Et | Et | —(CH$_2$)$_3$— | 104~105 |
| 23 | Ph-N(Et)-C(=O)- | 2 | Cl | 5 | H | — | H | Et | Et | —(CH$_2$)$_3$— | NMR(7) |
| 24 | Ph-N(i-Pr)-C(=O)- | 2 | Cl | 3 | H | — | H | Et | Et | —(CH$_2$)$_3$— | 113~114 |
| 25 | Ph-N(i-Pr)-C(=O)- | 2 | Cl | 4 | H | — | H | Et | Et | —(CH$_2$)$_3$— | 129~130 |
| 26 | Ph-N(i-Pr)-C(=O)- | 2 | Cl | 5 | H | — | H | Et | Et | —(CH$_2$)$_3$— | 98~99 |
| 27 | Ph-N(i-Pr)-C(=O)- | 2 | NO$_2$ | 4 | H | — | H | Et | Et | —(CH$_2$)$_3$— | 137~139 |
| 28 | Ph-N(i-Pr)-C(=O)- | 2 | NH$_2$ | 4 | H | — | H | Et | Et | —(CH$_2$)$_3$— | 105~106 |
| 29 | Ph-CH=CH-CH$_2$-NH-C(=O)- | 2 | Cl | 5 | H | — | H | Et | Et | —(CH$_2$)$_3$— | NMR(8) |

TABLE 1-continued

| | | | | | | | | | | | |
|---|---|---|---|---|---|---|---|---|---|---|---|
| 30 | Ph-NH-C(O)- (phenyl) | 2 | H | — | H | — | H | Et | Et | —(CH$_2$)$_3$— | 128~129 |
| 31 | Ph-NH-C(O)- (phenyl) | 2 | Cl | 3 | H | — | H | Et | Et | —(CH$_2$)$_3$— | 108~110 |
| 32 | Ph-NH-C(O)- (phenyl) | 2 | Cl | 4 | H | — | H | Et | Et | —(CH$_2$)$_3$— | 148.5~150 |
| 33 | Ph-NH-C(O)- (phenyl) | 2 | Cl | 5 | H | — | H | Et | Et | —(CH$_2$)$_3$— | 103~105 |
| 34 | Cl-C$_6$H$_4$-NH-C(O)- (phenyl) | 2 | Cl | 3 | H | — | H | Et | Et | —(CH$_2$)$_3$— | 116~117 |
| 35 | MeO-C$_6$H$_4$-NH-C(O)- (phenyl) | 2 | Cl | 3 | H | — | H | Et | Et | —(CH$_2$)$_3$— | 124~126 |
| 36 | Bn-NH-C(O)- (phenyl) | 2 | Cl | 3 | H | — | H | Et | Et | —(CH$_2$)$_3$— | 138~139 |
| 37 | H$_2$N-C(O)- (phenyl) | 2 | H | — | H | — | H | Et | Et | —(CH$_2$)$_3$— | 137~139 |
| 38 | H$_2$N-C(O)- (phenyl) | 2 | Cl | 3 | H | — | H | Et | Et | —(CH$_2$)$_3$— | 100~101 |
| 39 | Me-NH-C(O)- (phenyl) | 2 | Cl | 5 | H | — | H | Et | Et | —(CH$_2$)$_4$— | NMR(4) |
| 40 | Me-NH-C(O)- (phenyl) | 2 | Cl | 3 | H | — | H | Et | Et | —(CH$_2$)$_4$— | 89~91 |
| 41 | Me-NH-C(O)- (phenyl) | 2 | Cl | 5 | H | — | H | Et | Et | —(CH$_2$)$_5$— | NMR(5) |
| 42 | Me-NH-C(O)- (phenyl) | 2 | Cl | 5 | H | — | H | Et | Et | —(CH$_2$)$_7$— | NMR(6) |

TABLE 1-continued

| # | Structure | | | | | | | | | mp (°C) |
|---|---|---|---|---|---|---|---|---|---|---|
| 43 | Ph-CH2-N(Me)-C(=O)- | 2 | Cl | 3 | H | — | H | i-Pr | i-Pr | —(CH₂)₃— | 105~107 |
| 44 | Ph-CH2-N(Me)-C(=O)- | 2 | Cl | 5 | H | — | H | Et | Et | —CH(CH₃)— | 135~136 |
| 45 | Ph-CH2-N(Me)-C(=O)- | 2 | Cl | 5 | H | — | H | Et | Et | —CH₂— | 146.5~148.0 |
| 46 | Ph-CH2-N(Ph)-C(=O)- | 2 | Cl | 5 | H | — | H | Et | Et | —(CH₂)₂— | 148.5~149.5 |
| 47 | Ph-CH2-N(Me)-C(=O)- | 2 | Cl | 5 | H | — | H | Et | Et | —(CH₂)₂— | 148.5~149.5 |
| 48 | Ph-CH2-N(Me)-C(=O)- | 4 | H | — | H | — | H | Et | Et | —(CH₂)₃— | 138~139 |
| 49 | Ph-CH2-N(Me)-C(=O)- | 3 | Me | 2 | H | — | H | Et | Et | —(CH₂)₃— | 107~108 |
| 50 | Ph-CH2-N(Me)-C(=O)- | 4 | Cl | 3 | H | — | H | Et | Et | —(CH₂)₃— | 130.5~131.5 |
| 51 | Ph-CH2-N(Me)-C(=O)- | 2 | Cl | 5 | H | — | H | Et | Et | single bond | 112.5~113.5 |
| 52 | Ph-CH2-N(Me)(Me)-C(=O)- | 2 | Cl | 3 | H | — | H | Et | Et | —(CH₂)₃— | 59~60 |
| 53 | Ph-CH2-N(4-Me-piperazinyl)-C(=O)- | 2 | Cl | 3 | H | — | H | Et | Et | —(CH₂)₃— | NMR(9) |
| 54 | 3,5-diCl-Ph-NH-C(=O)- | 2 | Cl | 3 | H | — | H | Et | Et | —(CH₂)₃— | 145~147 |
| 55 | Ph-CH2-N(Me)-C(=O)- | 2 | Cl | 5 | H | — | Me | Et | Et | —CH₂— | NMR(10) |

TABLE 1-continued

| | | | | | | | | | | | |
|---|---|---|---|---|---|---|---|---|---|---|---|
| 56 | Ph-N(Me)-C(=O)- (with NH) | 2 | Cl | 5 | H | — | Bn | Et | Et | —CH$_2$— | NMR(11) |

| Example | $^1$H-NMR (δ: ppm) |
|---|---|
| No. 1 NMR(1) | 1.31(t, 6H, J=8.4Hz), 1.8–1.9(m, 2H), 2.0–2.1(m. 2H), 2.59(t, 2H, J=7.2Hz), 2.99(d, 3H, J=5.0Hz), 4.0–4.2(m, 4H), 6.53(br.s, 1H), 7.03(dd, 1H, J=2.0, 8.4Hz), 7.39(d, 1H, J=8.4Hz), 8.69(d, 1H, J=2.0Hz), 11.30(br.s, 1H) |
| No. 2 NMR(2) | 1.33(t, 6H, J=7.2Hz), 1.8–2.1(m, 4H), 2.51(t, 2H, J=7.2Hz), 2.99(d, 3H, J=4.5Hz), 4.0–4.2(m, 4H), 6.54(br.s, 1H), 7.0–7.1(m, 1H), 7.4–7.5(m, 2H), 8.56(d, 1H, J=8.4Hz), 11.16(br.s, 1H) |
| No. 21 NMR(3) | 1.32(t, 6H, J=6.7Hz), 1.8–2.1(m, 4H), 2.51(t, 2H, J=6.9Hz), 2.98(d, 3H, J=2.0Hz), 3.87(s, 3H), 3.94(s, 3H), 4.0–4.2(m, 4H), 6.27(br.s, 1H), 6.90(s, 1H), 8.38(s, 1H), 11.41(br.s, 1H) |
| No. 39 NMR(4) | 1.31(t, 6H, J=7.2Hz), 1.7–1.9(m, 6H), 2.42(t, 2H, J=7.2Hz), 2.98(d, 3H, J=4.9Hz), 4.0–4.2(m, 4H), 6.85(br.s, 1H), 6.99(dd, 1H, J=2.8, 8.4Hz), 7.41(d, 1H, J=8.4Hz), 8.66(d, 1H, J=2.0Hz), 11.33(br.s, 1H) |
| No. 41 NMR(5) | 1.31(t, 6H, J=7.2Hz), 1.5–1.8(m, 8H), 2.41(t, 2H, J=7.4Hz), 2.99(d, 3H, J=4.5Hz), 4.0–4.1(m, 4H), 6.57(br.s, 1H), 7.06(dd, 1H, J=2.0, 8.4Hz), 7.39(d, 1H, J=8.4Hz), 8.70(d, 1H, J=2.0Hz), 11.26(br.s, 1H) |
| No. 42 NMR(6) | 1.31(t, 6H, J=6.9Hz), 1.6–1.7(m, 12H), 2.40(t, 2H, J=7.4Hz), 3.00(d, 3H, J=5.0Hz), 4.0–4.1(m, 4H), 6.72(br.s, 1H), 7.00(dd, 1H, J=2.0, 8.4Hz), 7.39(d, 1H, J=8.4Hz), 8.70(d, 1H, J=2.0Hz), 11.21(br.s, 1H) |
| No. 23 NMR(7) | 1.27(t, 3H, J=7.2Hz), 1.33(t, 6H, J=7.1Hz), 1.8–2.2(m, 4H), 2.51(t, 2H, J=7.2Hz), 3.4–3.5(m, 2H), 4.0–4.2(m, 4H), 6.64(br.s, 1H), 7.01(dd, 1H, J=2.2, 8.4Hz), 7.42(d, 1H, J=8.4Hz), 8.67(d, 1H, J=2.2Hz), 11.34(br.s, 1H) |
| No. 29 NNR(8) | 1.33(t, 6H, J=7.1Hz), 1.8–2.1(m, 4H), 2.51(t, 2H, J=7.2Hz), 4.0–4.2(m, 6H), 5.24(s, 1H), 5.30(s, 1H), 5.9–6.0(m, 1H), 6.67(br.s, 1H), 7.03(dd, 1H, J=2.0, 8.4Hz), 7.46(d, 1H, J=8.4Hz), 8.71(d, 1H, J=2.0Hz), 11.29(br.s, 1H) |
| No. 53 NMR(9) | 1.33(t, 6H, J=7.1Hz), 1.8–2.1(m, 4H), 2.17(br.s, 4H), 2.31(s, 3H), 2.3–2.6(m, 4H), 3.2–3.4(m, 2H), 3.7–3.8 (m, 1H), 3.9–4.2(m, 5H), 7.18(d, 1H, J=7.9Hz), 7.31(t, 1H, J=7.9Hz), 7.88(d, 1H, J=7.9Hz), 8.11(br.s, 1H) |
| No. 55 NMR(10) | 1.25, 1.36(each t, J=6.9Hz, total 6H), 2.8–3.5(m, 2H), 2.91(d, J=4.0Hz, 3H), 3.17(s, 3H), 3.9–1.4, 1–4.3 (each m, total 4H), 7.19(s, 1H), 7.40(d, J=8.4Hz, 1H), 7.61(d, J=8.4Hz, 1H), 8.4(br.s, 1H) |
| No. 56 NMR(11) | 1.25, 1.36(each t, J=6.9Hz, total 6H), 2.8–3.2(m, 2H), 2.86(d, J=3.5Hz, 3H), 3.9–4.1, 4.1–4.3(each m, total 4H), 5.38(d, J=14.3Hz, 2H), 6.82(d, J=2.0Hz, 1H), 7.1–7.4(m, 6H), 7.55(d, J=7.9Hz, 1H), 7.9(br.s, 1H) |

FORMULATION EXAMPLE 1

Preparation of Tablets

Tablets (2000 tablets) containing a compound of the present invention obtained in Example 31 as an active ingredient (300 mg per tablet) were prepared according to the following recipe.

| | |
|---|---|
| a compound of the present invention obtained in Example 31 | 600 g, |
| lactose (Japanese Pharmacopoeia) | 67 g, |
| corn starch (Japanese Pharmacopoeia) | 33 g, |
| carboxymethylcellulose calcium (Japanese Pharmacopoeia) | 25 g, |
| methylcellulose (Japanese Pharmacopoeia) | 12 g, |
| magnesium stearate (Japanese Pharmacopoeia) | 3 g. |

That is, according to the above recipe, the compound of the present invention obtained in Example 31 was fully mixed with lactose, corn starch and carboxymethylcellulose calcium. The mixture was granulated with methylcellulose aqueous solution and passed through a 24-mesh screen. The granules were mixed with magnesium stearate and the mixture was compressed to give the desired tablets.

FORMULATION EXAMPLE 2

Preparation of Capsules

Hard gelatin capsules (2000 capsules) containing a compound of the present invention obtained in Example 8 as an active ingredient (200 mg per capsule) were prepared according to the following recipe.

| | |
|---|---|
| a compound of the present invention obtained in Example 8 | 400 g, |
| crystalline cellulose (Japanese Pharmacopoeia) | 60 g, |
| corn starch (Japanese Pharmacopoeia) | 34 g, |
| talc (Japanese Pharmacopoeia) | 4 g, |
| magnesium stearate (Japanese Pharmacopoeia) | 2 g. |

That is, according to the above recipe, each of the components was ground to a powder and they were mixed together to give a uniform mixture. Oral gelatin capsules of appropriate size were filled with the mixture to obtain the desired capsules.

PHARMACOLOGICAL TEST EXAMPLE

The compounds of the present invention were tested for blood glucose-lowering activities in rats in the following manner.

That is, Dexamethasone (Decadron S injectable solution-:made by Banyu Pharmaceutical Co.,Ltd.) was administered intraperitoneally to a group (test group) of 5 male Wister rats (6 weeks old) at a daily dose of 0.5 mg/kg, once a day for 4 days. Immediately after the administration of dexamethasone, a test compound (100 mg/kg) dissolved in 5% gum arabic solution was administered orally to rats daily. On day 4, the rats were decapitated 4 hours after the administration of dexamethasone. Blood was collected and centrifuged (3000 rpm, 4, 15 minutes), then the glucose level in the obtained serum was measured by the use of Glucose cII Test Wako (made by Wako Pure Chemical Industries, Ltd.). The rats were maintained on a diet ad libitum and then fasted 24 hours before the collection of blood.

Animals which were given 5% gum arabic solution instead of a test compound were served as a control group and those which were maintained merely on a diet ad libitum were served as a normal group. The serum glucose levels of them were measured according to the same manner as above. The decrease rate of blood glucose level was determined by the value (mean value) of each group from the following equation.

Decrease Rate (%) in Blood Glucose Level =

$$100 \times \frac{\text{(the value of control group)} - \text{(the value of test group)}}{\text{(the value of control group)} - \text{(the value of normal group)}}$$

Results obtained are shown in the following Table 2.

TABLE 2

| Test compound (Example No.) | Decrease rate (%) in blood glucose level | Test compound (Example No.) | Decrease rate (%) in blood glucose level |
|---|---|---|---|
| 4 | 20 | 25 | 17 |
| 5 | 31 | 31 | 59 |
| 7 | 30 | 32 | 16 |
| 8 | 39 | 36 | 12 |
| 9 | 30 | 38 | 18 |
| 12 | 15 | 40 | 14 |
| 14 | 44 | 44 | 21 |
| 15 | 50 | 51 | 17 |
| 16 | 22 | 54 | 13 |
| 19 | 24 | ↓ | ↓ |

In the same manner as Example 1, the compounds shown in the following Table 3 are obtained.

TABLE 3

(1)

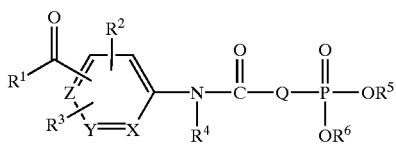

| No | Y=X / Z | $R^1$—C(=O)— | Position of Substituent | $R^2$ | Position of Substituent | $R^3$ | Position of Substituent | $R^4$ | $R^5$ | $R^6$ | Q |
|---|---|---|---|---|---|---|---|---|---|---|---|
| 57 | 2-pyridyl | Me—NH—C(=O)— | 3 | H | — | H | — | Me | Et | Et | —CH$_2$— |
| 58 | phenyl | Et—NH—C(=O)— | 2 | Me | 3 | H | — | H | Et | Et | —CH$_2$— |
| 59 | phenyl | CH$_2$=CH—NH—C(=O)— | 2 | Me | 3 | H | — | H | Et | Et | —(CH$_2$)$_3$— |
| 60 | 4-pyridyl | Me—NH—C(=O)— | 2 | Br | 3 | H | — | H | Et | Et | —(CH$_2$)$_3$— |
| 61 | phenyl | Bu—NH—C(=O)— | 2 | Cl | 3 | H | — | H | Et | Et | —CH$_2$— |
| 62 | 2-pyridyl | Me—NH—C(=O)— | 2 | F | 3 | H | — | H | Et | Et | —(CH$_2$)$_3$— |

TABLE 3-continued

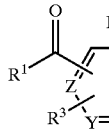

(1)

| No | Z-Y=X ring | R¹—C(O)— | Position of Substituent | R² | Position of Substituent | R³ | Position of Substituent | R⁴ | R⁵ | R⁶ | Q |
|---|---|---|---|---|---|---|---|---|---|---|---|
| 63 | 2-pyridyl | Et-NH-C(O)- | 3 | H | — | H | — | H | Et | Et | —(CH₂)₃— |
| 64 | phenyl | Me-NH-C(O)- | 2 | NH₂ | 4 | H | — | Et | Et | Et | —(CH₂)₃— |
| 65 | phenyl | Et-NH-C(O)- | 2 | MeSO₂NH | 2 | H | — | H | Et | Et | —(CH₂)₃— |
| 66 | 2-pyridyl | allyl-NH-C(O)- | 3 | H | — | H | — | H | Et | Et | —(CH₂)₃— |
| 67 | phenyl | Me-NH-C(O)- | 2 | H | — | H | — | H | i-Pr | i-Pr | —(CH₂)₃— |
| 68 | phenyl | Me-NH-C(O)- | 2 | Cl | 3 | H | — | H | Et | Et | —(CH₂)₅— |
| 69 | phenyl | Me-NH-C(O)- | 2 | H | 5 | H | — | H | Et | Et | —(CH₂)₅— |
| 70 | phenyl | i-Pr-NH-C(O)- | 2 | MeO | 4 | MeO | 5 | H | i-Pr | i-Pr | —CH₂— |
| 71 | phenyl | Et-NH-C(O)- | 2 | Br | 3 | Br | 5 | Me | Et | Et | —(CH₂)₄— |
| 72 | phenyl | Me-NH-C(O)- | 2 | Cl | 3 | H | — | H | Me | Et | —(CH₂)₃— |

TABLE 3-continued (1)

Structure: R¹-C(=O)-[ring with Z=X, Y=X, R², R³]-N(R⁴)-C(=O)-Q-P(=O)(OR⁵)(OR⁶)

| No | Z=Y, Y=X ring | R¹-C(=O)- | Position of Substituent | R² | Position of Substituent | R³ | Position of Substituent | R⁴ | R⁵ | R⁶ | Q |
|----|---|---|---|---|---|---|---|---|---|---|---|
| 73 | phenyl | Et-NH-C(=O)- | 2 | H | — | H | — | Me | Me | Me | —(CH₂)₃— |
| 74 | phenyl | Me-NH-C(=O)- | 3 | Me | 2 | H | — | Me | Et | Et | — |
| 75 | phenyl | Et-N(piperazinyl)-C(=O)- | 2 | H | — | H | — | H | Et | Et | —(CH₂)₃— |
| 76 | phenyl | Me-NH-C(=O)- | 2 | Cl | 4 | Cl | 6 | H | Me | Et | —(CH₂)₃— |
| 77 | phenyl | i-Pr-NH-C(=O)- | 2 | H | — | H | — | Bn | Et | Et | —(CH₂)₃— |
| 78 | pyridyl | Me-NH-C(=O)- | 2 | NO₂ | 5 | H | — | Bn | Et | Et | —(CH₂)₃— |
| 79 | phenyl | Me-NH-C(=O)- | 2 | F | 4 | F | 6 | H | Et | Et | —(CH₂)₄— |
| 80 | pyridyl | Bu-NH-C(=O)- | 2 | F | 3 | H | — | H | Et | Et | —(CH₂)₂— |
| 81 | phenyl | allyl-NH-C(=O)- | 2 | NO₂ | 4 | H | — | Me | Et | Et | —CH₂— |
| 82 | phenyl | Me-NH-C(=O)- | 2 | Cl | 3 | Cl | 5 | H | Me | Et | —(CH₂)₂— |
| 83 | pyridyl | Me-NH-C(=O)- | 2 | Br | 3 | Me | 6 | Me | Et | Et | —(CH₂)₄— |

TABLE 3-continued (1)

[Structure: R¹-C(=O)-[ring with Z,Y,X and R³]-CR²=CH-N(R⁴)-C(=O)-Q-P(=O)(OR⁵)(OR⁶)]

| No | Z〈Y=X〉 | R¹−C(=O)− | Position of Substituent | R² | Position of Substituent | R³ | Position of Substituent | R⁴ | R⁵ | R⁶ | Q |
|---|---|---|---|---|---|---|---|---|---|---|---|
| 84 | phenyl | 3-F-C₆H₄-NH-C(=O)- | 2 | H | — | H | — | H | Et | Et | —(CH₂)₃— |
| 85 | 2-pyridyl | Me-NH-C(=O)- | 2 | H | — | H | — | Bn | Et | Et | —(CH₂)₃— |
| 86 | phenyl | Et-NH-C(=O)- | 2 | H | — | H | — | i-Pr | Et | Et | —(CH₂)₃— |
| 87 | phenyl | Me-NH-C(=O)- | 2 | C₂H₅SO₂NH | 4 | H | — | Me | Et | Et | —(CH₂)₃— |
| 88 | phenyl | Me-NH-C(=O)- | 2 | H | — | H | — | H | Me | Me | —(CH₂)₃— |
| 89 | phenyl | Me-NH-C(=O)- | 2 | C₂H₅SO₂NH | 4 | H | — | H | Et | Et | —(CH₂)₃— |
| 90 | 2-pyridyl | Me-NH-C(=O)- | 2 | Cl | 3 | H | — | Me | Et | Et | — |
| 91 | phenyl | Me-NH-C(=O)- | 2 | Cl | 4 | Cl | 6 | H | Et | Et | — |
| 92 | 4-pyridyl | Me-NH-C(=O)- | 2 | H | — | H | — | H | Et | Et | —CH(CH₃)— |
| 93 | phenyl | Me-NH-C(=O)- | 2 | NH₄ | 4 | H | — | i-Pr | Et | Et | —(CH₂)₃— |

TABLE 3-continued (1)

| No | Z Y=X | R¹—C(O)— | Position of Substituent | R² | Position of Substituent | R³ | Position of Substituent | R⁴ | R⁵ | R⁶ | Q |
|---|---|---|---|---|---|---|---|---|---|---|---|
| 94 | 2-pyridyl | Et-NH-C(O)- | 3 | Me | 2 | H | — | H | Et | Et | —CH(CH₃)— |
| 95 | phenyl | 3-Cl-C₆H₄-NH-C(O)- | 2 | Cl | 3 | H | — | H | Et | Et | —(CH₂)₃— |
| 96 | phenyl | 3,5-diF-C₆H₃-NH-C(O)- | 2 | H | — | H | — | H | Et | Et | —(CH₂)₃— |
| 97 | phenyl | 3-Cl-C₆H₄-NH-C(O)- | 2 | Br | 3 | H | — | H | Et | Et | —(CH₂)₃— |
| 98 | phenyl | Me-NH-C(O)- | 2 | MeO | 6 | H | — | i-Pr | Et | Et | —(CH₂)₃— |
| 99 | 2-pyridyl | 3-F-C₆H₄-NH-C(O)- | 2 | H | — | H | — | H | Et | Et | —(CH₂)₃— |
| 100 | phenyl | 3,5-diF-C₆H₃-NH-C(O)- | 2 | H | — | H | — | H | Et | Et | —(CH₂)₃— |
| 101 | phenyl | 3,5-diCl-C₆H₃-NH-C(O)- | 2 | Me-C(O)-NH— | 4 | H | — | Me | Et | Et | —(CH₂)₃— |

$R^2$ for No. 101: Me—C(O)—NH—

INDUSTRIAL UTILIZATION OF THE INVENTION

Phosphonic acid diester derivatives of the present invention are effective for the prophylaxis or treatment of diabetes and are useful as medicines for human or animal.

The present invention has been described in detail including the preferred embodiments. However, it should be understood that those skilled in the art may make modifications and improvements within the spirit and scope of the invention.

What is claimed is:

1. A method of treating diabetes which comprises administering to a diabetic patient a diabetes treatment effective amount of a phosphonic acid diester derivative represented by the general formula:

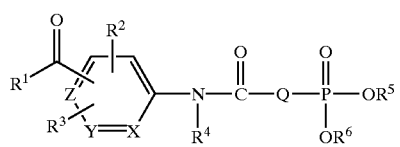

(1)

wherein:
$R^1$ represents an amino group, a N-lower alkylamino group, a N-lower alkenylamino group, a N-phenylamino group, a N-phenylamino group whose benzene ring are substituted with 1 or 2 groups being selected from a halogen atom and a lower alkoxy group, a N-phenyl(lower)alkylamino group, a N,N-di(lower)alkylamino group or a 4-lower alkylpiperazinyl group;

$R^2$ and $R^3$ each independently represent a hydrogen atom, a lower alkyl group, a halogen atom, a lower alkoxy group, a nitro group, an amino group, a N-lower alkylsulfonylamino group or a N-lower alkanoylamino group;

$R^4$ represents a hydrogen atom, a lower alkyl group or a phenyl(lower)alkyl group;

$R^5$ and $R^6$ each independently represent a lower alkyl group;

X, Y and Z each are carbon atoms or one of them is nitrogen atom and the other two are carbon atoms; and Q represents a single bond or an alkylene group;

or a pharmacologically acceptable salt thereof.

2. The method of claim 1, wherein X, Y and Z are simultaneously carbon atoms; or X is nitrogen atom and both Y and Z are carbon atoms.

3. The method of claim 2, wherein X, Y and Z are simultaneously carbon atoms.

4. The method of claim 3, wherein the phosphonic acid diester derivative is represented by the general formula:

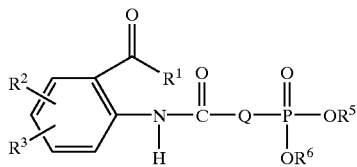

wherein $R^1$, $R^2$, $R^3$, $R^5$, $R^6$ and Q have the same meanings as set forth hereinbefore, or the pharmacologically acceptable salt thereof.

5. The method of claim 4, wherein $R^2$ and/or $R^3$ is a lower alkyl group, a halogen atom or a nitro group.

6. The method of claim 5, wherein Q is trimethylene group.

7. The method of claim 6, wherein $R^2$ is a halogen atom and $R^3$ is a hydrogen atom or a halogen atom.

8. The method of claim 7, wherein the phosphonic acid diester derivative is one selected from diethyl 3-(N-(3,5-dichloro-2-(N-methylcarbamoyl)phenyl)carbamoyl)-propylphosphonate, diethyl 3-(N-(4,6-dichloro2-(N-methylcarbamoyl)phenyl)carbamoyl)-propylphosphonate and diethyl 3-(N-(3-chloro-2-(N-phenylcarbamoyl)phenyl) carbamoyl)propyl-phosphonate, or the pharmacologically acceptable salt thereof.

9. An pharmaceutical composition for the prophylaxis or treatment of diabetes containing an effective amount of at least one compound as an active ingredient together with a nontoxic carrier, wherein the compound is a phosphonic acid diester derivative represented by the general formula:

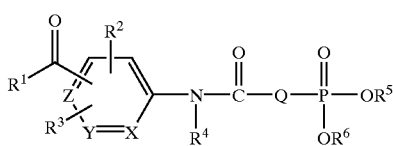

(1)

wherein:
$R^1$ represents an amino group, a N-lower allylamino group, a N-lower alkenylamino group, a N-phenylamino group, a N-phenylamino group whose benzene ring are substituted with 1 or 2 groups being selected from a halogen atom and a lower alkoxy group, a N-phenyl(lower)alkylamino group, a N,N-di(lower)alkylamino group or a 4-lower alkylpiperazinyl group;

$R^2$ and $R^3$ each independently represent a hydrogen atom, a lower alkyl group, a halogen atom, a lower alkoxy group, a nitro group, an amino group, a N-lower alkylsulfonylamino group or a N-lower alkanoylamino group;

$R^4$ represents a hydrogen atom, a lower alkyl group or a phenyl(lower)alkyl group;

$R^5$ and $R^6$ each independently represent a lower alkyl group;

X, Y and Z each are carbon atoms or one of them is nitrogen atom and the other two are carbon atoms; and Q represents a single bond or an alkylene group;

or a pharmacologically acceptable salt thereof.

10. A method of lowering blood glucose which comprises administering to a patient a blood glucose lowering effective amount of a compound represented by the general formula:

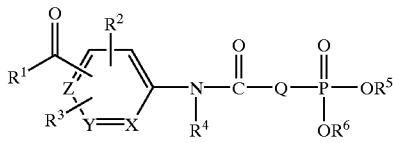

(1)

wherein:
$R^1$ represents an amino group, a N-lower alkylamino group, a N-lower alkenylamino group, a N-phenylamino group, a N-phenylamino group whose benzene ring are substituted with 1 or 2 groups being selected from a halogen atom and a lower alkoxy group, a N-phenyl(lower)alkylamino group, a N,N-di(lower)alkylamino group or a 4-lower alkylpiperazinyl group;

R² and R³ each independently represent a hydrogen atom, a lower alkyl group, a halogen atom, a lower alkoxy group, a nitro group, an amino group, a N-lower alkylsulfonylamino group or a N-lower alkanoylamino group;

R⁴ represents a hydrogen atom, a lower alkyl group or a phenyl(lower)alkyl group;

R⁵ and R⁶ each independently represent a lower alkyl group;

X, Y and Z each are carbon atoms or one of them is nitrogen atom and the other two are carbon atoms; and Q represents a single bond or an alkylene group;

or a pharmacologically acceptable salt thereof.

11. The pharmaceutical composition of claim 9, wherein X, Y and Z are simultaneously carbon atoms; or X is nitrogen atom and both Y and Z are carbon atoms.

12. The pharmaceutical composition of claim 11, wherein X, Y and Z are simultaneously carbon atoms.

13. The pharmaceutical composition of claim 12, wherein the phosphonic acid diester derivative is represented by the general formula:

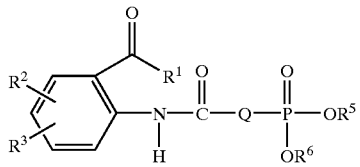

wherein R¹, R², R³, R⁵, R⁶ and Q have the same meanings as set forth hereinbefore, or the pharmacologically acceptable salt thereof.

14. the pharmaceutical composition of claim 13, wherein R² and/or R³ is a lower alkyl group, a halogen atom or a nitro group.

15. The pharmaceutical composition of claim 14, wherein Q is trimethylene group.

16. The pharmaceutical composition of claim 15, wherein R² is a halogen atom and R³ is a hydrogen atom or a halogen atom.

17. The pharmaceutical composition of claim 16, wherein the phosphonic acid diester derivative is selected from the group consisting of diethyl 3-(N-(3,5-dichloro-2-(N-methylcarbamoyl)phenyl)carbamoyl)propylphosphonate, diethyl 3-(N-(4,6-dichloro2-(N-methylcarbamoyl)phenyl)carbamoyl)propylphosphonate and diethyl 3-(N-(3-chloro-2-(N-phenylcarbamoyl)phenyl)carbamoyl)propylphosphonate, or is the pharmacologically acceptable salt of one of said group.

18. The method of claim 10, wherein X, Y and Z are simultaneously carbon atoms; or X is nitrogen atom and both Y and Z are carbon atoms.

19. The method of claim 18, wherein X, Y and Z are simultaneously carbon atoms.

20. The method of claim 19, wherein the phosphonic acid diester derivative is represented by the general formula:

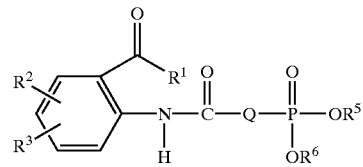

wherein R¹, R², R³, R⁵, R⁶ and Q have the same meanings as set forth hereinbefore, or the pharmacologically acceptable salt thereof.

21. The method of claim 20, wherein R² and/or R³ is a lower alkyl group, a halogen atom or a nitro group.

22. The method of claim 21, wherein Q is trimethylene group.

23. The method of claim 22, wherein R² is a halogen atom and R³ is a hydrogen atom or a halogen atom.

24. The method of claim 23, wherein the phosphonic acid diester derivative is selected from the group consisting of diethyl 3-(N-(3,5-dichloro-2-(N-methylcarbamoyl)phenyl) carbamoyl)propylphosphonate, diethyl 3-(N-(4,6-dichloro2-(N-methylcarbamoyl)phenyl)carbamoyl)propylphosphonate and diethyl 3-(N-(3-chloro-2-(N-phenylcarbamoyl)phenyl) carbamoyl)propyl-phosphonate, or is the pharmacologically acceptable salt of one of said group.

* * * * *